(12) United States Patent
Shirota et al.

(10) Patent No.: US 10,085,630 B2
(45) Date of Patent: Oct. 2, 2018

(54) ENDOSCOPE APPARATUS

(71) Applicant: OLYMPUS CORPORATION, Tokyo (JP)

(72) Inventors: Yutaka Shirota, Kawasaki (JP); Tomoya Takahashi, Hachioji (JP); Masato Toda, Hachioji (JP); Yusuke Yabe, Chofu (JP); Yusuke Yoshida, Fussa (JP); Aiko Sakai, Higashimurayama (JP); Takahiro Masaki, Kawasaki (JP); Takahiro Hayama, Hino (JP); Ryo Machida, Koza (JP); Koji Omori, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 114 days.

(21) Appl. No.: 15/142,507

(22) Filed: Apr. 29, 2016

(65) Prior Publication Data

US 2016/0235285 A1 Aug. 18, 2016

Related U.S. Application Data

(63) Continuation of application No. PCT/JP2014/078223, filed on Oct. 23, 2014.

(30) Foreign Application Priority Data

Oct. 30, 2013 (JP) ................................ 2013-225778

(51) Int. Cl.
*A61B 1/06* (2006.01)
*A61B 1/12* (2006.01)
(Continued)

(52) U.S. Cl.
CPC .......... *A61B 1/128* (2013.01); *A61B 1/00006* (2013.01); *A61B 1/04* (2013.01);
(Continued)

(58) Field of Classification Search
CPC ....... A61B 1/00025; A61B 1/12; A61B 1/128; H01L 33/64
(Continued)

(56) References Cited

U.S. PATENT DOCUMENTS 4,301,790 A * 11/1981 Bol ..................... A61B 1/00018
348/65
4,367,036 A * 1/1983 Sakamaki ............ G03G 21/203
355/30
(Continued)

FOREIGN PATENT DOCUMENTS

EP 2283769 A1 2/2011
JP H08-306226 A 11/1996
(Continued)

OTHER PUBLICATIONS

International Search Report dated Nov. 18, 2014 issued in PCT/JP2014/078223.
(Continued)

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

An endoscope apparatus includes: first and second cooling units configured to cool first and second light source portions; an image pickup portion configured to generate a picked-up image; and a cooling control portion configured to control amounts of light emission of the light source portions while maintaining an amount-of-light ratio so that the brightness of the picked-up image becomes the target brightness and control cooling based on the information about the amount-of-light ratio and the brightness control information; wherein the cooling control portion decides a cooling capacity of the first cooling units and a cooling capacity of the
(Continued)

second cooling units for cooling the respective light source portions for which the amounts of light emission are controlled, at the cooling ratio, so as to cause the light source portions to be included within a predetermined temperature range, based on the brightness control information.

5 Claims, 10 Drawing Sheets

(51) Int. Cl.
G02B 23/24 (2006.01)
G02B 27/14 (2006.01)
A61B 1/00 (2006.01)
A61B 1/04 (2006.01)
A61B 1/07 (2006.01)
H01L 33/64 (2010.01)

(52) U.S. Cl.
CPC .......... *A61B 1/0638* (2013.01); *A61B 1/0669* (2013.01); *A61B 1/0684* (2013.01); *A61B 1/07* (2013.01); *G02B 23/2461* (2013.01); *G02B 27/141* (2013.01); *H01L 33/64* (2013.01)

(58) Field of Classification Search
USPC .......................................... 600/178, 117, 118
See application file for complete search history.

(56) References Cited

U.S. PATENT DOCUMENTS

| | | | | |
|---|---|---|---|---|
| 5,076,660 | A * | 12/1991 | Messinger | A61B 1/07 385/119 |
| 6,322,496 | B1 * | 11/2001 | Iida | A61B 1/00039 348/74 |
| 6,464,633 | B1 * | 10/2002 | Hosoda | A61B 1/0638 348/68 |
| 7,137,696 | B2 * | 11/2006 | Siegel | B41F 23/0409 347/101 |
| 7,211,299 | B2 * | 5/2007 | Siegel | B41F 23/0409 118/620 |
| 7,942,548 | B2 * | 5/2011 | Kawachi | H05B 33/0803 362/244 |
| 8,002,415 | B2 * | 8/2011 | Nakamura | G03B 21/006 353/52 |
| 8,622,896 | B1 * | 1/2014 | Termanini | A61B 1/12 348/65 |
| 8,807,760 | B2 * | 8/2014 | Kanno | G03B 21/16 165/104.33 |
| 9,351,355 | B2 * | 5/2016 | Kim | H05B 33/0815 |
| 2002/0014595 | A1 * | 2/2002 | Sendai | A61B 1/00009 250/458.1 |
| 2003/0007087 | A1 * | 1/2003 | Hakamata | A61B 1/0638 348/370 |
| 2005/0201107 | A1 * | 9/2005 | Seki | G03B 21/16 362/373 |
| 2006/0120084 | A1 * | 6/2006 | Sueoka | G03B 21/16 362/294 |
| 2007/0247134 | A1 * | 10/2007 | Ryan | H02J 13/001 323/318 |
| 2008/0033240 | A1 * | 2/2008 | Hoffman | A61B 1/313 600/109 |
| 2010/0171935 | A1 * | 7/2010 | Yamagishi et al. | G03B 21/16 353/52 |
| 2011/0034770 | A1 * | 2/2011 | Endo | A61B 1/0638 600/118 |
| 2011/0071352 | A1 * | 3/2011 | Ozawa | A61B 1/0638 600/109 |
| 2011/0135170 | A1 * | 6/2011 | Wang | G06T 7/0012 382/128 |
| 2011/0172492 | A1 * | 7/2011 | Erikawa | A61B 1/0638 600/178 |
| 2013/0154509 | A1 * | 6/2013 | Yabe | A61B 1/00006 315/297 |
| 2013/0286175 | A1 * | 10/2013 | Hashimoto | A61B 1/0638 348/68 |
| 2013/0334966 | A1 * | 12/2013 | Kumano | G03B 21/16 315/117 |
| 2014/0267657 | A1 * | 9/2014 | Takei | G02B 23/2469 348/68 |

FOREIGN PATENT DOCUMENTS

| | | | |
|---|---|---|---|
| JP | 2005-257873 | A | 9/2005 |
| JP | 2006-162653 | A | 6/2006 |
| JP | 2010-256558 | A | 11/2010 |
| JP | 2011-036361 | A | 2/2011 |
| JP | 2012-066015 | A | 4/2012 |

OTHER PUBLICATIONS

Japanese Office Action dated Feb. 2, 2016 issued in JP 2015-525322.

Extended Supplementary European Search Report dated Aug. 23, 2017 in European Patent Application No. 14 85 9050.8.

* cited by examiner (a)

(b)

ENDOSCOPE APPARATUS

CROSS REFERENCE TO RELATED APPLICATION

This application is a continuation application of PCT/JP2014/078223 filed on Oct. 23, 2014 and claims benefit of Japanese Application No. 2013-225778 filed in Japan on Oct. 30, 2013, the entire contents of which are incorporated herein by this reference.

BACKGROUND OF THE INVENTION

1. Field of the Invention

The present invention relates to an endoscope apparatus appropriate for an endoscope.

2. Description of the Related Art

Conventionally, endoscope apparatuses for performing observation of a site to be examined or various kinds of treatments by inserting an elongated endoscope into a body cavity or the like have been widely used. In such an endoscope apparatus, a light source apparatus is adopted to perform photographing inside the cavity. In recent years, there may be a case where a light source apparatus adopting a solid-state light-emitting element, such as an LED and a laser light source, as a light emitting portion is used. Such a light source apparatus can perform light adjustment control of the LED by PWM control for changing a duty ratio of a driving pulse or current control for changing an LED current.

By using solid-state light-emitting elements in a plurality of colors as solid-state light-emitting elements, such as LEDs and laser light sources, it is possible for the light source apparatus to emit illuminating light with arbitrary color balance. For example, Japanese Patent Application Laid-Open Publication No. 2011-36361 discloses an apparatus in which it is possible to change color balance of illuminating light with use of blue and violet laser light sources. In the case of a light source apparatus with LEDs also, it is similarly possible to radiate illuminating light having arbitrary color balance, for example, by adopting LEDs for respective colors of R, G and B.

Note that a light source apparatus for endoscope is required to emit a large amount of illuminating light. Therefore, an amount of light emission of each solid-state light-emitting element is large, and an amount of heat generation is also large. The solid-state light-emitting element, however, has a temperature characteristic that light emission efficiency decreases as temperature increases. Therefore, in the light source apparatus using solid-state light-emitting elements, it is necessary to adopt a cooling apparatus for cooling the solid-state light-emitting elements. For example, cooling members, such as a fan, a heat sink, a heat pipe and a Peltier element, are used in the cooling apparatus. As for the cooling members which require power, for example, by supplying sufficient power corresponding to a maximum amount of heat generation of the solid-state light-emitting elements to the cooling members, each of the solid-state light-emitting elements is sufficiently cooled to prevent the light emission efficiency from decreasing.

By the way, each image pickup device provided for an endoscope differs in a spectral sensitivity characteristic. Further, each light guiding optical system provided in an endoscope so as to guide illuminating light from a light source apparatus to an object differs in a spectral transmission characteristic. Therefore, in a case of using one light source apparatus for a plurality of kinds of endoscopes, it is necessary to adjust color balance of illuminating light according to the spectral sensitivity characteristic and spectral transmission characteristic of each endoscope. That is, it is necessary to cause an amount-of-light ratio, which is a ratio of amounts of light emission of light emitted from the solid-state light-emitting elements for the respective colors of the light source apparatus, to be changed according to the spectral sensitivity characteristic and spectral transmission characteristic of the endoscope. Further, color balance of required illuminating light differs in different observation modes, for example, a normal-light observation mode for performing observation using white color light, a special-light observation mode for obtaining particular information about an object by radiating light with a predetermined wavelength different from white color light to the object, and the like, and, therefore, it is necessary to cause the amount-of-light ratio of the solid-state light-emitting elements to change for the respective colors.

SUMMARY OF THE INVENTION

An endoscope apparatus according to one aspect of the present invention includes: a first light source portion configured to generate light; a second light source portion configured to generate light; first cooling means configured to cool the first light source portion; second cooling means configured to cool the second light source portion; a light guiding portion configured to be inserted into a subject and configured to be capable of guiding the light from the first light source portion and the light from the second light source portion and capable of emitting the guided light from a distal end; an image pickup portion configured to receive light from the subject to which the lights emitted from the distal end of the light guiding portion is radiated to generate a picked-up image; a generation portion configured to generate brightness control information for causing brightness of the picked-up image to be target brightness; and a cooling control portion configured so that information about an amount-of-light ratio, which is a ratio of an amount of the light emitted by the second light source portion to an amount of the light emitted by the first light source portion, and the brightness control information are inputted and configured to control amounts of light emission of the first light source portion and the second light source portion while maintaining an amount-of-light ratio corresponding to the information about the amount-of-light ratio so that the brightness of the picked-up image generated by the image pickup portion becomes the target brightness and control the first cooling means and the second cooling means based on the information about the amount-of-light ratio and the brightness control information; wherein the cooling control portion identifies information about a cooling ratio, which is a ratio for performing cooling by the first cooling means and cooling by the second cooling means, based on the information about the amount-of-light ratio; decides a cooling capacity of the first cooling means and a cooling capacity of the second cooling means for cooling the first light source portion and the second light source portion for which the amounts of light emission are controlled so that the brightness of the picked-up image becomes the target brightness, at the cooling ratio, so as to cause the first light source portion and the second light source portion to be included within a predetermined temperature range, based on the brightness control information; and controls the first cooling means and the second cooling means to be driven with the cooling capacities decided for the first cooling means and the second cooling means.

DETAILED DESCRIPTION OF THE PREFERRED EMBODIMENTS

Embodiments of the present invention will be described below in detail with reference to drawings.

(First Embodiment)

Figure 1:
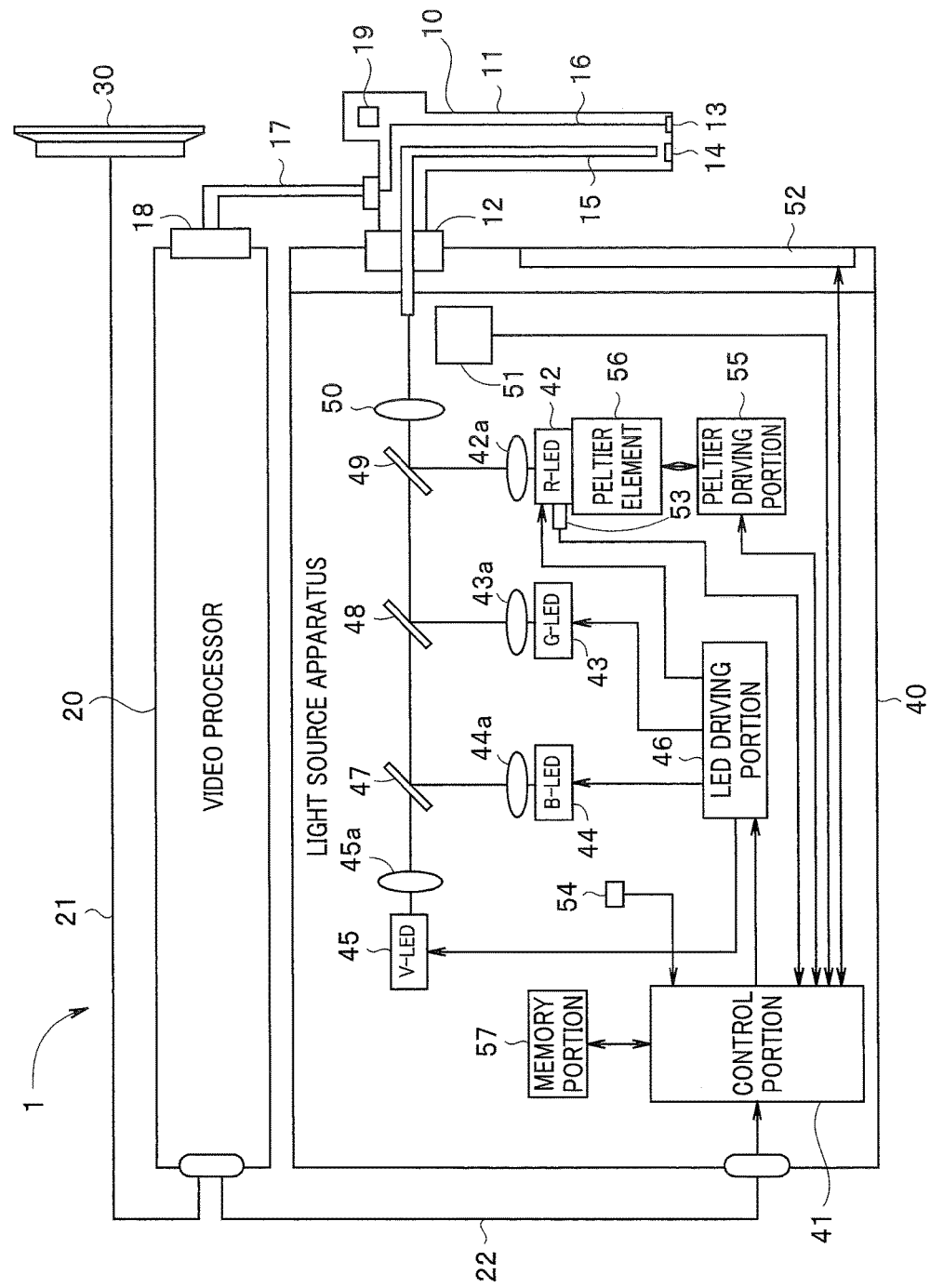
FIG. 1 is a block diagram showing a light source apparatus according to a first embodiment of the present invention.

FIG. 1 is a block diagram showing a light source apparatus according to a first embodiment of the present invention. The present embodiment is such that the light source apparatus is applied to an endoscope apparatus having an endoscope, a video processor and a monitor.

An endoscope apparatus 1 is configured with an endoscope 10, a video processor 20, a monitor 30 and a light source apparatus 40. The endoscope 10 has an elongated insertion portion 11 which can be inserted into a lumen and the like at a distal end side, and its proximal end side is adapted to be detachably connected to the light source apparatus 40 via a connector 12.

Further, the endoscope 10 is adapted to be detachably connected to the video processor 20 via a cable 17 and a connector 18. Thus, different kinds of endoscopes can be connected to the light source apparatus 40 and the video processor 20.

An image pickup device 13 for picking up video of an object in a lumen or the like and a lens 14 for radiating light from the light source apparatus 40 to the object are arranged at a distal end of the insertion portion 11. Illuminating light transmitted from the light source apparatus 40 via a light guide 15 is radiated to the object by the lens 14. The image pickup device 13 is configured with a CCD sensor, a CMOS sensor or the like. Return light from the object is caused to be incident on an image pickup surface of the image pickup device 13, and the image pickup device 13 performs photoelectric conversion of an incident object optical image and sequentially outputs image pickup outputs based on accumulated charges.

The image pickup device 13 operates by being supplied with a driving signal which includes a synchronization signal, from the video processor 20, and supplies an image pickup output to the video processor 20 via a signal line 16.

The video processor 20 performs predetermined signal processing for the supplied image pickup output to generate a video signal which can be displayed on the monitor 30. The video signal from the video processor 20 is supplied to the monitor 30 via a cable 21. Thus, an endoscopic image based on the image pickup output can be displayed on a display screen of the monitor 30.

Further, the video processor 20 is adapted to be capable of controlling the light source apparatus 40 so that brightness of a picked-up image becomes target brightness. The video processor 20 is adapted to output information about a ratio of the brightness obtained from the picked-up image to the target brightness to the light source apparatus 40 as brightness control information. The brightness control information is supplied to a control portion 41 of the light source apparatus 40 via a cable 22, and the light source apparatus 40 controls an amount of illuminating light based on the brightness control information.

Note that, though FIG. 1 shows an example in which the video processor 20 and the light source apparatus 40 are configured as separate bodies, the video processor 20 and the light source apparatus 40 may be integrated with each other. Further, it is also possible for the light source apparatus 40 to acquire the information about the ratio of the information about the brightness obtained from the picked-up image to the target brightness as the brightness control information.

The light source apparatus 40 has a plurality of solid-state light-emitting elements which emit lights in different colors, such as an LED (R-LED) 42 which generates red color light, an LED (G-LED) 43 which generates green color light, an LED (B-LED) 44 which generates blue color light and an LED (V-LED) 45 which generates violet color light. Note that, though description will be made on an example in which LEDs generating four colors are adopted in the present embodiment, the kinds of colors and the number of colors are not limited to those of the present embodiment. For example, an LED generating another color may be added to FIG. 1, and the solid-state light-emitting elements may not be LEDs but laser light sources. Further, though one LED is provided for each color in the present embodiment, this is not limiting, and a plurality of solid-state light-emitting elements may be provided for each color.

Lenses 42a to 45a are arranged on optical axes of emitted lights of the respective LEDs 42 to 45, respectively. The respective lenses 42a to 45a convert the emitted lights of the LEDs 42 to 45, respectively, to substantially parallel lights and emit the substantially parallel lights. Dichroic filters 47 to 49 constituting an optical path portion are arranged on an optical axis of the lens 45a which emits light from the V-LED 45. Light from the B-LED 44 is also caused to be incident on the dichroic filter 47 via the lens 44a. Light from the G-LED 43 is also caused to be incident on the dichroic filter 48 via the lens 43a, and light from the R-LED 42 is also caused to be incident on the dichroic filter 49 via the lens 42a.

The dichroic filter 47 reflects blue color light from the B-LED 44 and causes violet color light from the V-LED 45 to be transmitted. The dichroic filter 48 reflects green color light from the G-LED 43 and causes synthesized light obtained by combining the violet color light and the blue color light from the dichroic filter 47 to be transmitted. The dichroic filter 49 reflects red color light from the R-LED 42 and causes synthesized light obtained by combining the violet color light, blue color light and green color light from the dichroic filter 48 to be transmitted.

Note that, in order to obtain emitted light in a desired color, each dichroic filter may cut light of a part of wavelength of incident light to perform transmission and reflection instead of transmitting/reflecting the entire wavelength of the incident light.

In this way, the violet color light, blue color light, green color light and red color light of the LEDs 42 to 45 are combined by the dichroic filters 47 to 49. Light synthesized by the respective color lights from the dichroic filter 49 is caused to be incident on the light guide 15 of the endoscope 10 via a lens 50. Note that, though it is possible to change arrangement order of the LEDs 42 to 45 by appropriately setting characteristics of the dichroic filters 47 to 49, it is easier to set the characteristics of the dichroic filters 47 to 49 if the LEDs 42 to 45 are arranged in order of wavelength bands of emitted lights.

Each of the LEDs 42 to 45 is driven and lit up by an LED driving portion 46. The LED driving portion 46 is adapted to be controlled by the control portion 41 to generate, for example, a driving signal with a PWM pulse for driving each LED. Each of the LEDs 42 to 45 is adapted to emit light with an amount of light emission corresponding to a duty ratio and amount of current of the PWM pulse of the driving signal for the LED supplied from the LED driving portion 46. The control portion 41 controls the duty ratio and current level of the PWM pulse to perform light adjustment control of the amount of light emission of each of the LEDs 42 to 45, by outputting the above-mentioned brightness control information for controlling each of the LEDs 42 to 45 and light adjustment information including amount-of-light ratio control information to be described later to the LED driving portion 46.

The control portion 41 generates the amount-of-light ratio control information, which is information about an amount-of-light ratio of the respective LEDs 42 to 45 so that the light synthesized by the respective color lights caused to be incident on the light guide 15 from the dichroic filter 49 is in a predetermined color and that the respective LEDs 42 to 45 are caused to emit light so that predetermined color balance can be maintained. It is necessary to decide the amount-of-light ratio of the respective LEDs 42 to 45 by a spectral sensitivity characteristic and spectral transmission characteristic of the endoscope 10 to be used.

The image pickup device 13 provided in the endoscope 10 has a predetermined spectral sensitivity characteristic. Further, not only the spectral transmission characteristic of the image pickup device but also a spectral transmission characteristic of the light guide 15, which is a light guiding optical system, differs for each endoscope 10 to be used. The endoscope 10 is provided with a storage portion 19 which stores the amount-of-light ratio control information, which is information about the ratio of the amount of light emission (the amount-of-light ratio) of the respective LEDs, in consideration of such a spectral sensitivity characteristic and spectral transmission characteristic. By causing each LED to emit light with an amount of light emission based on the amount-of-light ratio control information, illuminating light from the light source apparatus 40 can be set to color balance suitable for the endoscope 10.

That is, driving of each LED is controlled so that brightness of a picked-up image becomes target brightness based on the brightness control information while the amount-of-light based on the amount-of-light ratio control information is obtained.

Figure 2:
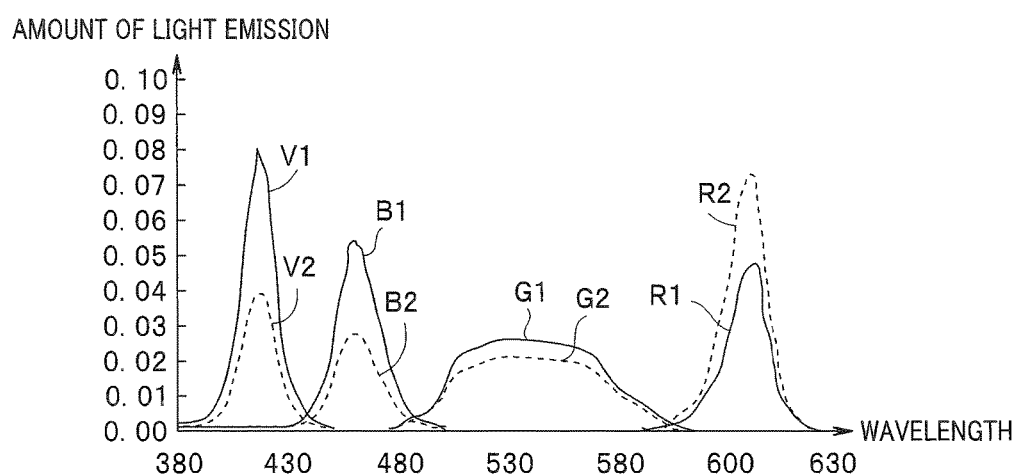
FIG. 2 is a graph showing amounts of light emission of each LED required to obtain white color light suitable for two endoscopes as emitted light, in which a wavelength and an amount of light emission are indicated by a horizontal axis and a vertical axis, respectively.

FIG. 2 is a graph showing amounts of light emission of each LED required to obtain white color light suitable for two endoscopes as emitted light, in which a wavelength and an amount of light emission are indicated by a horizontal axis and a vertical axis, respectively. A solid line indicates an amount of light emission for a predetermined first endoscope, and V1, G1, B1 and R1 indicate amounts of light emission of violet, green, blue and red LEDs, respectively. A broken line in FIG. 2 indicates an amount of light emission required for a predetermined second endoscope, and V2, G2, B2 and R2 indicate amounts of light emission of violet, green, blue and red LEDs, respectively. As shown in FIG. 2, amounts of light emission of each LED required to obtain white color light suitable for the first and second endoscopes differ from each other, and, for example, for the red color and violet color LEDs, difference between the amounts of light emission is large.

Figure 3:
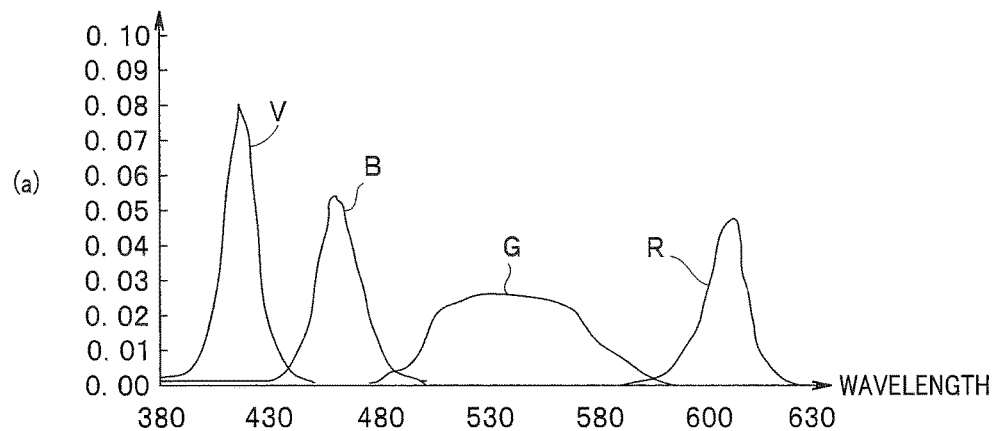
FIG. 3 is a graph showing an amount of light emission of each LED required to obtain illuminating light suitable for two observation modes as emitted light, in which a wavelength and an amount of light emission are indicated by a horizontal axis and a vertical axis, respectively.
Figure 3:
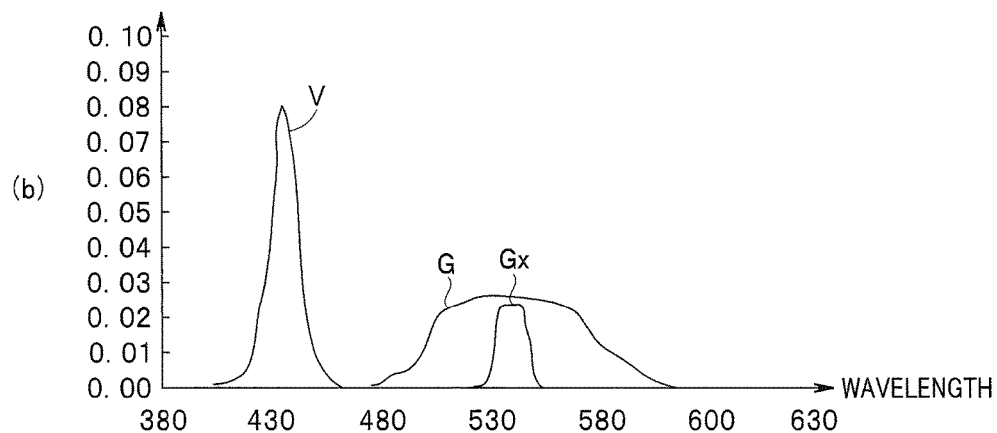

Note that an endoscope enabling not only normal-light observation but also special-light observation may be adopted as the endoscope 10. FIG. 3 is a graph showing an amount of light emission of each LED required to obtain illuminating light suitable for two observation modes as emitted light, in which a wavelength and an amount of light emission are indicated by a horizontal axis and a vertical axis, respectively. FIG. 3(a) shows the amount of light emission in the normal-light observation mode, and FIG. 3(b) shows the amount of light emission in a narrow-band-light observation mode. As shown in FIGS. 3(a) and 3(b), the amounts of light emission of each LED required to obtain illuminating light suitable for the normal-light observation mode and the narrow-band-light observation mode, respectively, differ from each other. In narrow-band-light observation, it is only necessary to cause only the violet color and green color LEDs among the four color LEDs to emit light. In the storage portion 19, information about the amount-of-light ratio for each observation mode is also stored.

Note that, in the narrow-band-light observation shown in FIG. 3(b), a filter not shown may be inserted on an optical path of the light of G in order to cause a wavelength range of the light of G, which is caused to be incident on the light guide 15 of the endoscope 10 from the dichroic filter 49, to be a narrow-band wavelength range as indicated by Gx.

Further, in addition to the synchronous endoscope for performing the normal-light observation by radiating white color light, there may be a case where a frame-sequential endoscope in which, for example, R, G and B illuminating lights are sequentially radiated, and a color image is generated from frame-sequentially obtained images is adopted. In a case of supplying illuminating light to such a frame-sequential endoscope, it is necessary to sequentially light up, for example, respective R, G and B LEDs. In this case also, for the frame-sequential endoscope, by causing information about an amount-of-light ratio of the respective LEDs to be sequentially lit up to be stored in the storage portion 19 of the endoscope 10, it is possible to perform illumination with optimum color balance.

The light source apparatus 40 is provided with a reading portion 51, and the reading portion 51 is adapted to be capable of acquiring the amount-of-light ratio information from the storage portion 19, for example, by connecting the endoscope 10 to the light source apparatus 40 via the connector 12. The reading portion 51 outputs the read amount-of-light ratio information to the control portion 41. The control portion 41 is adapted to decide the amount of light emission of each of the LEDs 42 to 45 based on the amount-of-light ratio information and control the amount of light emission of each of the LEDs 42 to 45 so that the amount-of-light ratio is maintained.

Note that, though description has been made on an assumption that the reading portion 51 is provided for the light source apparatus 40, it is also possible to provide the reading portion 51 for the video processor 20 so that the control portion 41 acquires information from the video processor 20. Further, in order to obtain optimum color balance, it is only necessary to input amount-of-light ratio information suitable for the endoscope 10 to the control portion 41, and it is not necessarily required to provide the storage portion 19 and the reading portion 51. A memory for storing amount-of-light ratio information about each endoscope may be provided in the light source apparatus 40. Further, the light source apparatus 40 is provided with an operation panel 52, and the operation panel 52 is capable of outputting a signal based on a user operation to the control portion 41. It is also possible to input the amount-of-light ratio information about the endoscope 10 by using the operation panel 52. Further, the operation panel 52 is provided with a display portion not shown so that current set values and the like can be displayed.

Furthermore, there may be a case where an endoscope not holding such amount-of-light ratio information is adopted as the endoscope 10. In this case, since the light source apparatus 40 cannot acquire the amount-of-light ratio information for obtaining appropriate color balance, the control portion 41 may be adapted to control the amount of light emission of each of the LEDs 42 to 45 so that a predetermined amount-of-light ratio is obtained.

The control portion 41 controls of the amount of light emission of each of the LEDs 42 to 45 while maintaining an amount-of-light ratio at which the optimum color balance is obtained, based on brightness control information from the video processor 20. For example, by causing light adjustment information corresponding to an amount-of-light value of the G-LED 43 to be set according to the brightness control information to be stored in a memory portion 57, and reading the light adjustment information stored in the memory portion 57 based on the brightness control information, the light adjustment information for controlling the G-LED 43 can be acquired. Furthermore, the control portion 41 is capable of determining light adjustment information about the other LEDs 42, 44 and 45 based on the amount-of-light ratio information.

In the present embodiment, a Peltier element 56, which is a thermoelectric conversion element for cooling, is attached to the R-LED 42. The R-LED 42 has a substrate and a light emitting portion arranged on the substrate, which are not shown, and the Peltier element 56 is arranged, for example, on a back side of the substrate. The Peltier element 56 is a cooling member utilizing heat receiving and heat radiating phenomena generated by a current flowing through a pn junction, and is adapted to cool the R-LED 42 by causing a cooling surface of the Peltier element 56 to be in contact with a back of the substrate of the R-LED 42.

A cooling capacity of the Peltier element 56 varies according to a current value of a driving current flowing through the Peltier element 56. A Peltier driving portion 55 is adapted to control cooling of the R-LED 42 by being controlled by the control portion 41 to control the current value of the driving current caused to flow through the Peltier element 56. Note that, as for the R-LED 42, light emission efficiency is lower in comparison with the other the LEDs 43 to 45, power required to obtain a sufficient amount of light emission is high, and an amount of heat generation is larger in comparison with the other the LEDs 43 to 45. Therefore, though FIG. 1 shows an example in which the Peltier element 56 is arranged only for the R-LED 42, the other LEDs may be provided with Peltier elements.

In the present embodiment, the control portion 41 is adapted to cause the respective LEDs 42 to 45 to be maintained within a predetermined temperature range while preventing wasteful power consumption, by performing cooling control according to the amounts of heat generation of the respective LEDs 42 to 45.

For such temperature control, information about cooling characteristics of the respective LEDs (hereinafter referred to as cooling characteristic information) determined based on information about the light emission efficiency (the amounts of heat generation) of the respective LEDs 42 to 45 and information about cooling capacities of respective cooling members for cooling the respective LEDs is stored in the memory portion 57. The control portion 41 determines information showing at which ratio the respective LEDs are to be cooled (hereinafter referred to as cooling ratio information) based on the amount-of-light ratio information and the cooling characteristic information. Note that the control portion 41 may determine the cooling ratio information by calculation between the amount-of-light ratio information and the cooling characteristic information. Further, since the cooling characteristic information is information specific to the light source apparatus 40 and is already known, it is possible to store a table showing correspondence between the amount-of-light ratio and the cooling ratio information in consideration of the cooling characteristic information (hereinafter referred to as a cooling ratio table) in the memory portion 57. In this case, the control portion 41 can acquire cooling ratio information by referring to the cooling ratio table based on amount-of-light ratio information.

The control portion 41 determines cooling capacities required for the respective LEDs based on the brightness control information and the cooling ratio information and determines driving powers for driving cooling members such as the Peltier element 56 and respective fans to be described later so that the cooling capacities can be obtained.

Note that, though the above description has been made on an assumption that the cooling characteristic information is stored in the memory portion 57, and power supply for the cooling members is determined by calculating a cooling ratio based on the amount-of-light ratio information and the cooling characteristic information, the pieces of information may be externally inputted instead of being stored. Furthermore, instead of using the amount-of-light ratio information and cooling characteristic information themselves, amount-of-light control and cooling control may be performed using information corresponding to or related to the information. For example, in the light source apparatus, since the characteristics of the respective LEDs and characteristics of the cooling members for cooling the respective LEDs are already known, it is also possible to perform amount-of-light control and cooling control using information about a model number of an endoscope related to the amount-of-light ratio information, information related to the amount-of-light ratio information such as information indicating which observation mode is used, or the like. That is, the information related to the amount-of-light ratio includes the information about the model number of an endoscope, the information about which observation mode is selected and the like also, in addition to the amount-of-light ratio information and information corresponding to the amount-of-light ratio, and the control portion 41 can perform amount-of-light ratio control and cooling control using the information related to the amount-of-light ratio.

The control portion 41 outputs a control signal to the Peltier driving portion 55 to give driving power based on a cooling capacity required for the R-LED 42 to the Peltier element 56. Thereby, a driving current according to an amount of heat generation corresponding to the amount of light emission of the R-LED 42 flows through the Peltier element 56, and the Peltier element 56 demonstrates the desired cooling capacity.

When LEDs are used for illumination of an endoscope, amounts of light emission of the respective LEDs vary depending on a kind of the connected endoscope, an observation mode and the like. In the present embodiment, however, a cooling capacity of a cooling member corresponding to each LED is controlled for the LED, according to an amount of heat generation corresponding to an amount of light emission of the LED. Therefore, it is possible to prevent the cooling capacity for each LED from being insufficient or prevent each LED from being excessively cooled and to appropriately suppress increase in temperature by light emission of each LED.

Figure 4:
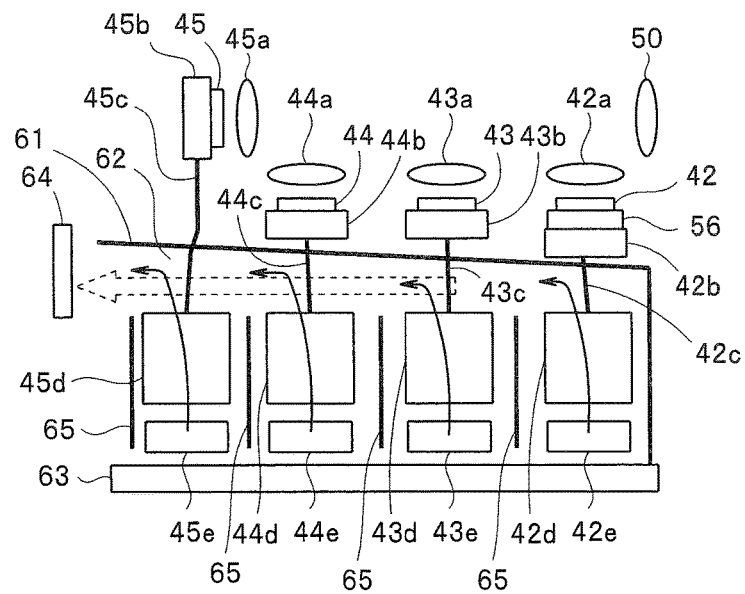
FIG. 4 is an explanatory diagram for illustrating an example of a cooling structure in the first embodiment.

FIG. 4 is an explanatory diagram for illustrating an example of a cooling structure in the present embodiment. As the cooling structure, a technique is conceivable in which heat sinks are provided for respective LEDs to radiate heat from the respective LEDs, and the heat sinks are arranged in a straight line from an inlet port to an exhaust port. In this case, however, air flowing in from the inlet port receives heat from the respective heat sinks and is warmed; and it is more difficult for a heat sink nearer to the exhaust port to radiate heat. Therefore, it is conceivable to increase a size of a heat sink nearer to the exhaust port. In this case, however, there is a demerit that the apparatus is upsized.

Therefore, in the present embodiment, a cooling structure in which air from an outside of a case is caused to flow for the heat sinks corresponding to the respective LEDs uniformly is adopted to prevent the sizes of the heat sinks from being restricted by distances from the inlet port.

The cooling surface of the Peltier element 56 abuts with the R-LED 42, and a heat radiating surface of the Peltier element 56 is in contact with a heat receiving member 42b. Heat receiving members 43b to 45b are directly in contact with the other LEDs 43 to 45, respectively. One end of the respective heat pipes 42c to 45c is attached to the heat receiving members 42b to 45b, respectively, and the other end of the respective heat pipes 42c to 45c is attached to the heat sinks 42d to 45d, respectively. The respective heat pipes 42c to 45c transmit heat received by the heat receiving members 42b to 45b to the heat sinks 42d to 45d, respectively. A separating wall 61 separating an interior of the light source apparatus 40 is provided between the heat sinks 42d to 45d and the respective heat receiving members 42b to 45b so that a heat radiation route 62 is configured on a heat sink side, and inflow of heat on an LEDs 42 to 45 side is prevented.

The heat radiation route 62 is separated into heat radiation routes for the respective LEDs 42 to 45 by walls 65. An inlet port 63 is provided on one face of the case of the light source apparatus 40 which faces the separating wall 61, and the heat sinks 42d to 45d are provided, corresponding to the respective LEDs 42 to 45, between the inlet port 63 and the separating wall 61. Fans 42e to 45e are provided, corresponding to the respective heat sinks 42d to 45d, between the respective heat sinks 42d to 45d and the inlet port 63. By the configuration, it is possible to cause air outside the case to flow directly to all of the heat sinks 42d to 45d corresponding to the respective LEDs 42 to 45 without causing the air to pass through the other heat sinks.

The air caused to flow into an inside of the case from the outside of the case via the inlet port 63 by the fans 42e to 45e receives heat from the heat sinks 42d to 45d and flows to a separating wall 61 side. Furthermore, the air which has received the heat from the heat sinks 42d to 45d changes its direction along inclination of the separating wall 61, flows toward an exhaust port 64 provided on another one face of the case, and is discharged to the outside of the case. Heat transmitted to the heat sinks 42d to 45d via the heat pipes 42c to 45c, respectively, is radiated via a heat radiation route (a broken line arrow) configured with a flow (an arrow) of air which flows in from the inlet port 63 and flows out from the exhaust port 64.

Cooling capacities are decided by characteristics of the Peltier element 56, the heat pipes 42c to 45c, the heat sinks 42d to 45d, the fans 42e to 45e and the like. For example, the cooling capacities vary depending on sizes of the heat sinks 42d to 45d and the fans 42e to 45e. Furthermore, as for the Peltier element 56 and the fans 42e to 45e, the cooling capacities vary depending on volume of inputted driving power. The memory portion 57 holds cooling characteristics information regarding the cooling capacities of the cooling members and the like, and the control portion 41 is adapted to be capable of calculating cooling characteristics based on the amount-of-light ratio information and the cooling characteristic information and calculating powers to be inputted to the Peltier element 56 and the fans 42e to 45e to obtain desired cooling capacities based on a calculation result. Further, if the cooling ratio table is stored in the memory portion 57, the control portion 41 can acquire cooling ratio information by referring to the cooling ratio table, based on the amount-of-light ratio information.

Note that dustproof filters may be provided between the inlet port 63 and the fans 42e to 45e. In this case, by varying roughness of dustproof filter mesh for each of the fans 42e to 45e to cause an amount of air inflow to differ for each fan, the cooling capacity for each LED can be controlled. Instead of the dustproof filter, various kinds of members for causing opening rates of the respective fans 42e to 45e at the inlet port 63 to vary may be used. For example, it is possible to arrange members made of punching metal or in a slit shape at the inlet port 63 and cause the opening rates of the members to vary for each of positions of the respective fans 42e to 45e.

Figure 5:
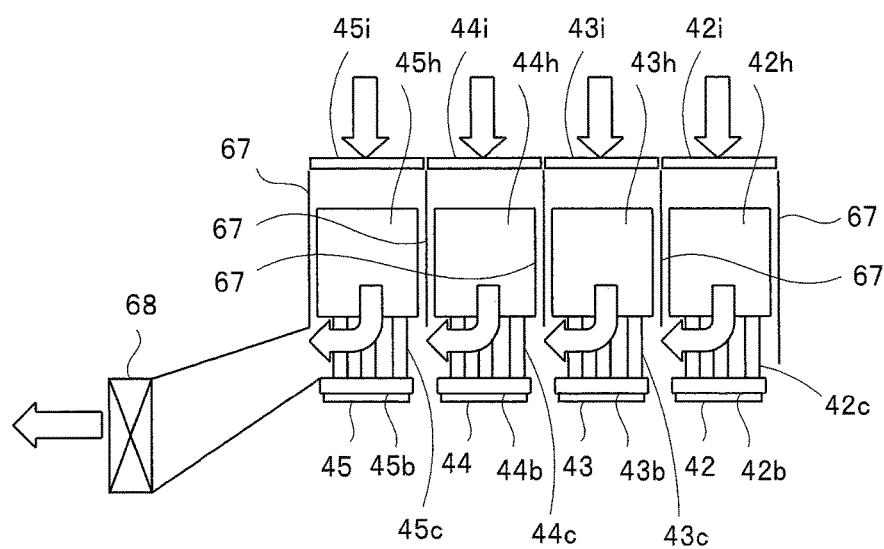
FIG. 5 is an explanatory diagram showing an example in which members made of punching metal or in a slit shape (hereinafter referred to as inflow control members) are used near an inlet port, and one fan is provided near an exhaust port.

FIG. 5 is an explanatory diagram showing an example in which members made of punching metal or in a slit shape (hereinafter referred to as inflow control members) are used near an inlet port, and one fan is provided near an exhaust port. In FIG. 5, heat radiation routes, which are air flow paths, are indicated by arrows. The LEDs 42 to 45 are attached to the heat receiving members 42b to 45b, and the heat receiving members 42b to 45b are connected to heat sinks 42h to 45h via the heat pipes 42c to 45c, respectively. The respective heat sinks 42h to 45h are mutually separated by walls 67 and arranged in independent flow paths. On an inlet port side, the inlet port being for causing air to flow into the respective heat sinks 42h to 45h, inflow control members 42i to 45i are arranged, respectively.

By a fan 68 arranged near an exhaust port rotating, air flows in via the inflow control members 42i to 45i. The inflow air receives heat of the heat sinks 42h to 45h in the respective independent flow paths and is discharged from the common exhaust port. Similarly to FIG. 4, all the heat sinks 42h to 45h are directly supplied with outside air which has not received heat from the other heat sinks and can sufficiently radiate heat. The inflow control members 42i to 45i are arranged at entrances of the respective flow paths. Therefore, by adjusting opening rates of the inflow control members 42i to 45i independently, it is possible to control the cooling capacities of the respective heat sinks 42h to 45h, and it is possible to adjust temperatures of the LEDs 42 to 45 independently.

In FIG. 1, the light source apparatus 40 is provided with thermistors 53 near the respective LEDs 42 to 45. Note that, in FIG. 1, only the thermistor 53 arranged near the R-LED 42 is shown for simplification of the drawing. The thermistors 53 measure temperatures of vicinities of the respective LEDs 42 to 45 and output a measurement result to the control portion 41. Further, the light source apparatus 40 is provided with a thermistor 54. The thermistor 54 is arranged at an appropriate position in the case of the light source apparatus 40. The thermistor 54 measures temperature of the inside of the case (room temperature) and outputs a measurement result to the control portion 41.

Figure 6:
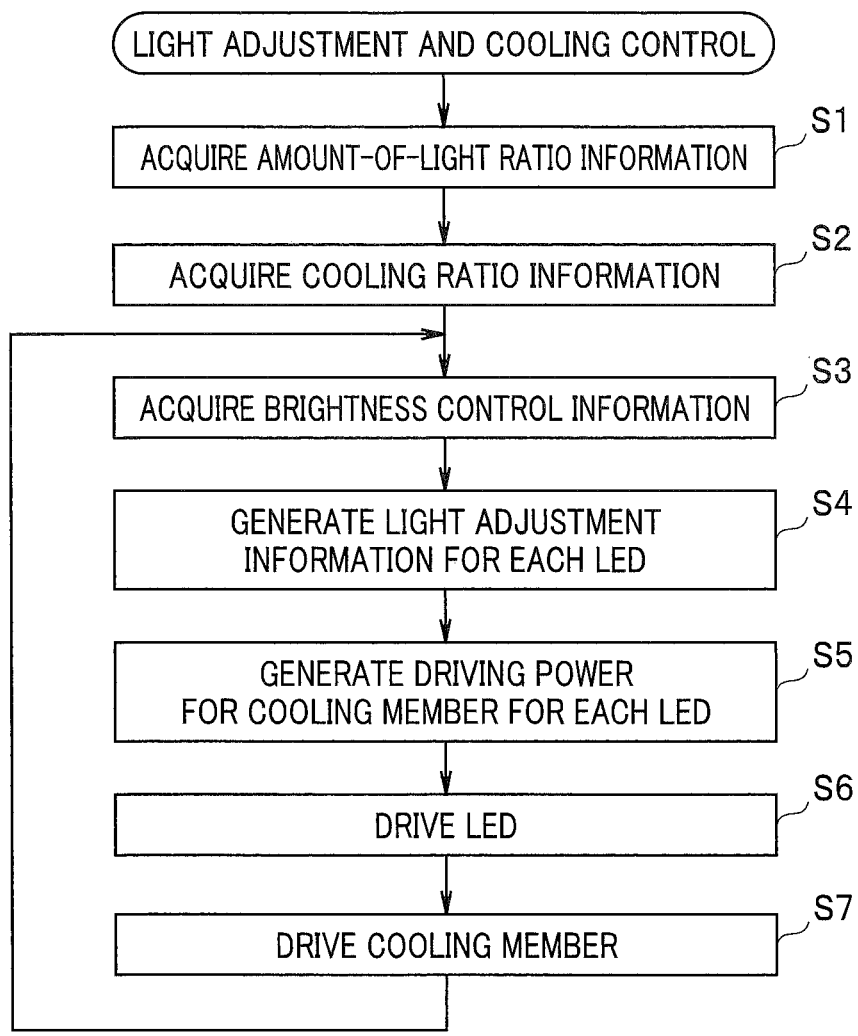
FIG. 6 is a flowchart for illustrating light adjustment control of the first embodiment.
Figure 7:
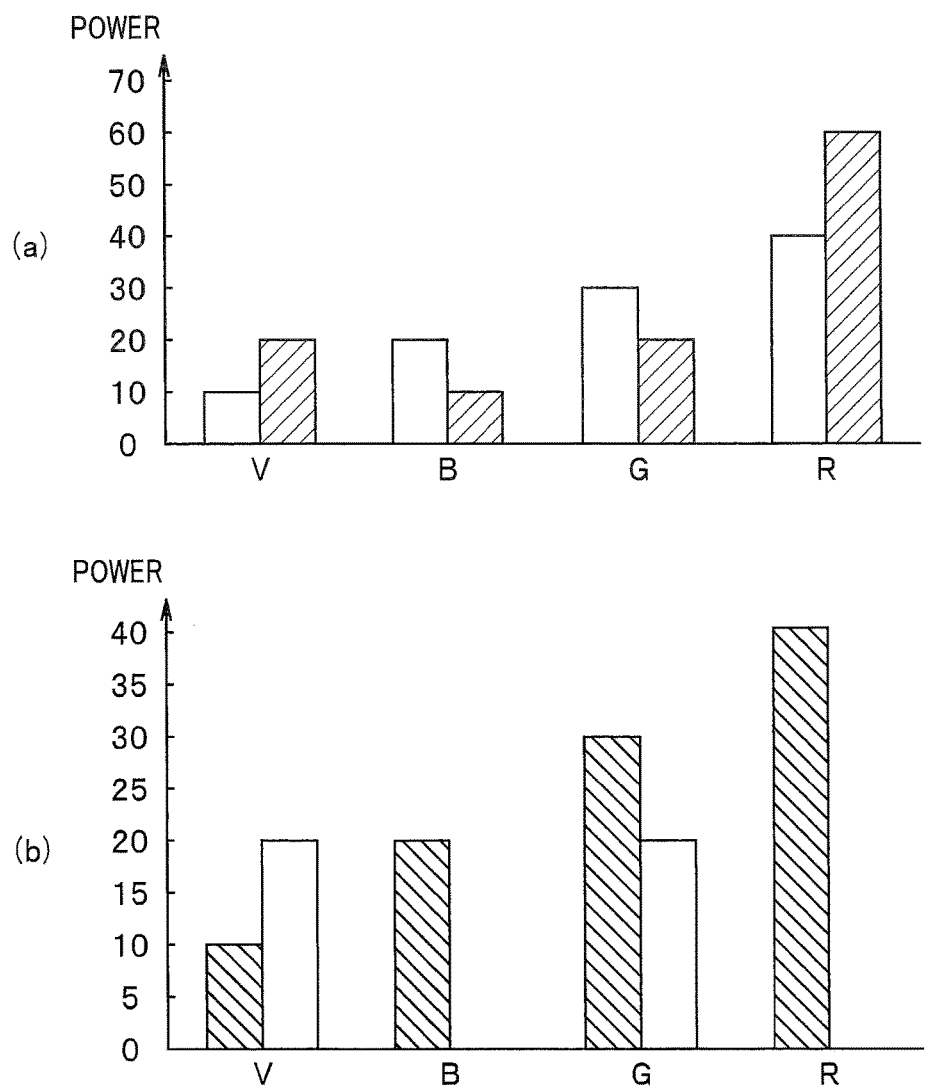
FIG. 7 is an explanatory diagram for illustrating powers supplied to fans and a Peltier element corresponding to respective LEDs in a case where two different endoscopes are used in a same observation mode and in a case where a same endoscope is used in the different observation modes.

Next, an operation of the embodiment configured as described above will be described with reference to FIGS. 6 and 7. FIG. 6 is a flowchart for illustrating light adjustment control of the first embodiment. FIG. 7 is an explanatory diagram for illustrating powers supplied to fans and a Peltier element corresponding to respective LEDs in a case where two different endoscopes are used in a same observation mode and in a case where a same endoscope is used in the different observation modes.

When the endoscope 10 is connected to the light source apparatus 40 via the connector 12, the reading portion 51 reads amount-of-light ratio information stored in the storage portion 19 of the endoscope 10 and outputs the amount-of-light ratio information to the control portion 41. Thereby, the control portion 41 acquires amount-of-light ratio information for each endoscope and for each observation mode (step S1). Further, the control portion 41 reads cooling ratio information by referring to the cooling ratio table stored in the memory portion 57 based on the amount-of-light ratio information (step S2).

At step S3, the control portion 41 acquires brightness control information from the video processor 20. The control portion 41 accesses the memory portion 57 based on the brightness control information to acquire control values (a current value and a duty ratio) for controlling the G-LED 43, which is a reference LED, and calculates control values for the other LEDs 42, 44 and 45 under an amount-of-light ratio based on the amount-of-light ratio information, with the control values for the LED 43 as reference values. The control portion 41 generates light adjustment information for specifying the control values determined for the respective LEDs 42 to 45 (step S4) and outputs the light adjustment information to the LED driving portion 46.

Further, at step S5, the control portion 41 calculates power to be supplied to each of the cooling members corresponding to the respective LEDs based on the amount-of-light values of the respective LEDs 42 to 45 and the cooling ratio information read from the memory portion 57.

The LED driving portion 46 generates PWM pulses having a duty ratio and a current value based on the light adjustment information and supplies the PWM pulses to the respective LEDs 42 to 45 (step S6). Thereby, the LEDs 42 to 45 generate light with an amount of light based on the light adjustment information. Emitted lights of the LEDs 42 to 45 are combined by the dichroic filters 47 to 49, and the light is caused to be incident on the light guide 15 via the lens 50 as illuminating light. The illuminating light transmitted through the light guide 15 is emitted to an object from the lens 14.

Further, the control portion 41 controls the Peltier driving portion 55 to drive the Peltier element 56 by the calculated power. Thereby, the Peltier driving portion 55 gives the determined power to the Peltier element 56 to cool the LEDs 42-45 (step S7).

Further, the control portion 41 controls power supply to the respective fans 42e to 45e so that the calculated powers are supplied to the respective fans 42e to 45e corresponding to the respective LEDs 42 to 45. Thereby, the respective fans 42e to 45e rotate by power supply to the fans 42e to 45e being individually controlled. Flow rates of air which receives heat of the heat sinks 42d to 45d corresponding to the respective LEDs 42 to 45 are individually controlled to control cooling for each LED.

Thus, powers for the cooling members corresponding to the respective LEDs 42 to 45 are controlled based on amounts of heat generation corresponding to amounts of generated light, and the cooling members suppress increase in temperatures of the respective LEDs 42 to 45 to enable operation within a predetermined temperature range. The cooling members corresponding to the respective LEDs 42 to 45 are individually controlled according to the amounts of heat generation, so that wasteful power consumption, noise and the like can be prevented.

The image pickup device 13 receives reflected light from the object and performs photoelectric conversion to obtain a picked-up image. The picked-up image is supplied to the video processor 20 via the signal line 16. The video processor 20 performs predetermined signal processing for the picked-up image to generate a video signal and supplies the video signal to the monitor 30 via the cable 21. In this way, an endoscopic image is displayed on the display screen of the monitor 30.

The video processor 20 generates brightness control information by comparing brightness of the picked-up image and target brightness. The control portion 41 updates the light adjustment information based on the brightness control information. After that, steps S3 to S7 are repeated, so that the amounts of light are controlled according to brightness based on the brightness control information, and cooling control is performed for the respective LEDs according to amounts of heat generation corresponding to the amounts of light.

Further, in the present embodiment, in a case where the endoscope connected to the light source apparatus 40 is switched, a case where the observation mode is varied in a same endoscope, and the like, it is possible to perform appropriate cooling control for each LED.

FIG. 7(*a*) shows power control of cooling members for two different endoscopes in a same observation mode, and FIG. 7(*b*) shows power control of cooling members in different observation modes of a same endoscope. In FIG. 7(*a*), plain bars indicate power control when a predetermined first endoscope is connected, and hatched bars indicate power control when a predetermined second endoscope is connected. Note that FIG. 7(*a*) shows power in a case of obtaining illuminating light with same color balance and same brightness in the first and second endoscopes. Further, the power shown in FIG. 7(*a*) indicates total power for a plurality of cooling members corresponding to respective LEDs. For example, as for an R-LED, total of powers supplied to a fan and a Peltier element is shown, and, as for the other LEDs, power supplied to a fan is shown.

As for the first endoscope in FIG. 7(*a*), it is shown that, when power is supplied to cooling members corresponding to a V-LED, a B-LED, a G-LED and the R-LED at a ratio of 1:2:3:4, cooling capacities for the respective LEDs are uniformed, and temperatures of the respective LEDs can be maintained within a predetermined temperature range. In the example of FIG. 7(*a*), it is shown that the cooling capacities for the respective LEDs are uniformed by supplying 10 W, 20 W, 30 W and 40 W to the cooling members corresponding to the V-LED, the B-LED, the G-LED and the R-LED of the first endoscope.

Further, as for the second endoscope in FIG. 7(*a*), it is shown that, when power is supplied to cooling members corresponding to a V-LED, a B-LED, a G-LED and the R-LED at a ratio of 2:1:2:6, cooling capacities for the respective LEDs are uniformed, and temperatures of the respective LEDs can be maintained within a predetermined temperature range. In the example of FIG. 7(*a*), it is shown that the cooling capacities for the respective LEDs are uniformed by supplying 20 W, 10 W, 20 W and 60 W to the cooling members corresponding to the V-LED, the B-LED, the G-LED and the R-LED of the second endoscope.

FIG. 7(*b*) shows power control of cooling members corresponding to respective LEDs in the different observation modes of the same endoscope. Hatched bars indicate power control in the normal-light observation mode, and plain bars indicate power control in the narrow-band-light observation mode. The power shown in FIG. 7(*b*) indicates total power for a plurality of cooling members corresponding to respective LEDs. For example, as for an R-LED, total of powers supplied to a fan and a Peltier element is shown, and, as for the other LEDs, power supplied to a fan is shown.

In the normal-light observation mode in FIG. 7(*b*), it is shown that, when power is supplied to cooling members corresponding to a V-LED, a B-LED, a G-LED and the R-LED at a ratio of 1:2:3:4, cooling capacities for the respective LEDs are uniformed, and temperatures of the respective LEDs can be maintained within a predetermined temperature range. In the example of FIG. 7(*b*), it is shown that, in the normal-light observation mode, the cooling capacities for the respective LEDs are uniformed by supplying 10 W, 20 W, 30 W and 40 W to the cooling members corresponding to the V-LED, the B-LED, the G-LED and the R-LED.

Further, in the narrow-band-light observation mode in FIG. 7(*b*), it is shown that, when power is supplied to cooling members corresponding to the V-LED, the B-LED, the G-LED and the R-LED at a ratio of 1:0:1:0, cooling capacities for the respective LEDs are uniformed, and temperatures of the respective LEDs can be maintained within a predetermined temperature range. In the example of FIG. 7(*b*), it is shown that, in the narrow-band-light-observation mode, only the V-LED and the G-LED are caused to be lit up, and the cooling capacities for the respective LEDs are uniformed by supplying 20 W to cooling members corresponding to the LEDs.

Thus, in the present embodiment, a cooling ratio of cooling members corresponding to respective LEDs is determined based on cooling characteristic information and amount-of-light ratio information obtained based on information about amounts of heat generation corresponding to amounts of light of the respective LEDs and information about cooling capacities of the respective cooling members for cooling the respective LEDs, and driving powers for the cooling members are decided so that the cooling ratio can be obtained. Thereby, it is possible to cause temperatures of the respective LEDs to be a desired temperature irrespective of the amounts of heat generation of the respective LEDs, and it is possible to prevent power from being wastefully consumed and prevent noise from being generated by fans being caused to wastefully rotate.

Note that, in the embodiment described above, an example has been shown in which, on an assumption that a correspondence relationship between amounts of heat generation of respective LEDs and cooling capacities of cooling members provided for the respective LEDs is constant and a cooling ratio does not change irrespective of brightness of illuminating light, that is, amounts of lights of the respective LEDs, powers inputted to the cooling members are linearly varied according to the amounts of lights of the respective LEDs. However, there is a possibility that the correspondence relationship between the amounts of heat generation of the respective LEDs and the cooling capacities of the cooling members provided for the respective LEDs may vary according to the amounts of light of the respective LEDs. Therefore, it is also possible to change power inputted to the cooling members while varying the cooling ratio in stages or continuously according to the amounts of light of the respective LEDs.

(Modification)

Figure 8:
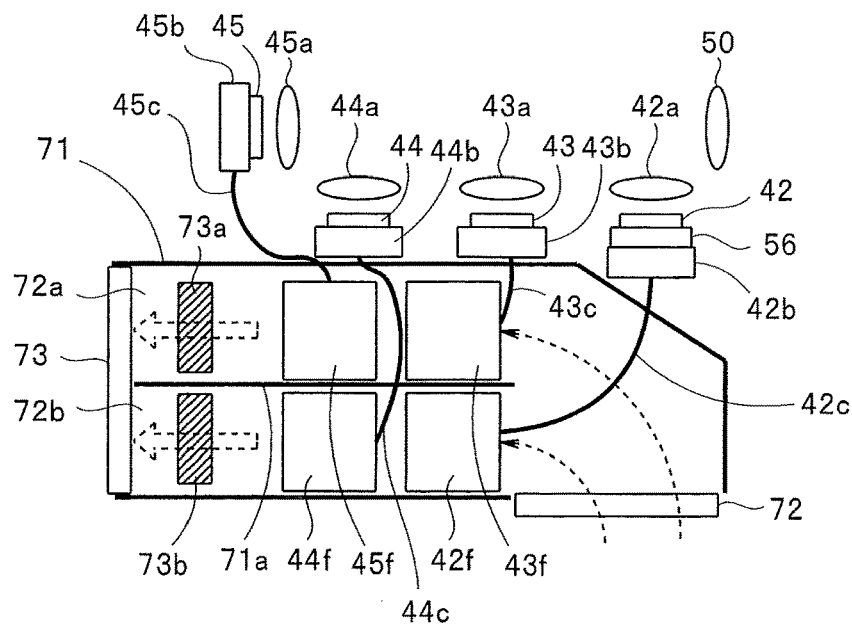
FIG. 8 is an explanatory diagram for illustrating another example of the cooling structure.

FIG. 8 is an explanatory diagram for illustrating another example of the cooling structure. In FIG. 8, same components as those in FIG. 4 are given same reference numerals, and description of the components will be omitted.

In the example of FIG. 8, an arrangement area of the respective LEDs 42 to 45 and a heat radiation route are separated by a separating wall 71 in a case of a light source apparatus. Furthermore, in the example of FIG. 8, a heat radiation route side is separated into two heat radiation routes 72*a* and 72*b* by a wall 71*a*. Heat sinks 43*f* and 45*f* are arranged on a heat radiation route 72*a* side, and heat sinks 42*f* and 44*f* are arranged on a heat radiation route 72*b* side. The heat sinks 42*f* and 45*f* are connected to the heat pipes 42*c* to 45*c*, respectively, so that heat generated by the respective LEDs 42 to 45 is transmitted.

An inlet port 72 is provided on one end side of one face of the case of the light source apparatus facing the separating wall 71, and an exhaust port 73 is provided on another face of the case. A face of the separating wall 71 facing the inlet port 72 has a surface inclined relative to an air inflow direction to cause an air flow to be toward an exhaust port 73 side. Note that the inclined surface may be a curved surface. In front of the exhaust port 73, fans 73a and 73b are provided at end portions of the heat radiation routes 72a and 72b, respectively, so that air which has flown in from the inlet port 72 can be forcedly caused to pass through the heat radiation routes 72a and 72b and caused to be discharged from the exhaust port 73, by rotation of the fans 73a and 73b.

Therefore, by individually controlling rotations of the fans 73a and 73b, it is possible to individually control heat radiation effects of the heat radiation routes 72a and 72b. That is, since the heat sinks 43f and 45f are arranged on the heat radiation route 72a side, and the heat sinks 42f and 44f are arranged on the heat radiation route 72b side, as described above, cooling capacities for a group of the V-LED 45 and the G-LED 43 and for a group of the B-LED 44 and the R-LED 42 can be individually controlled by the fans 73a and 73b.

For example, the fans 73a and 73b are caused to rotate at time of the normal-light observation; and, at time of the special-light observation, the fan 73b is caused to stop, and only the fan 73a is caused to rotate. At the time of the special-light observation, it is only required to cool only the group of the V-LED 45 and the G-LED 43 which are lit up, and, therefore, non-wasteful cooling control is possible. Note that it is apparent that the LEDs 42 to 45 can be individually controlled by controlling respective heat radiating members other than the fans 73a and 73b.

Figure 9:
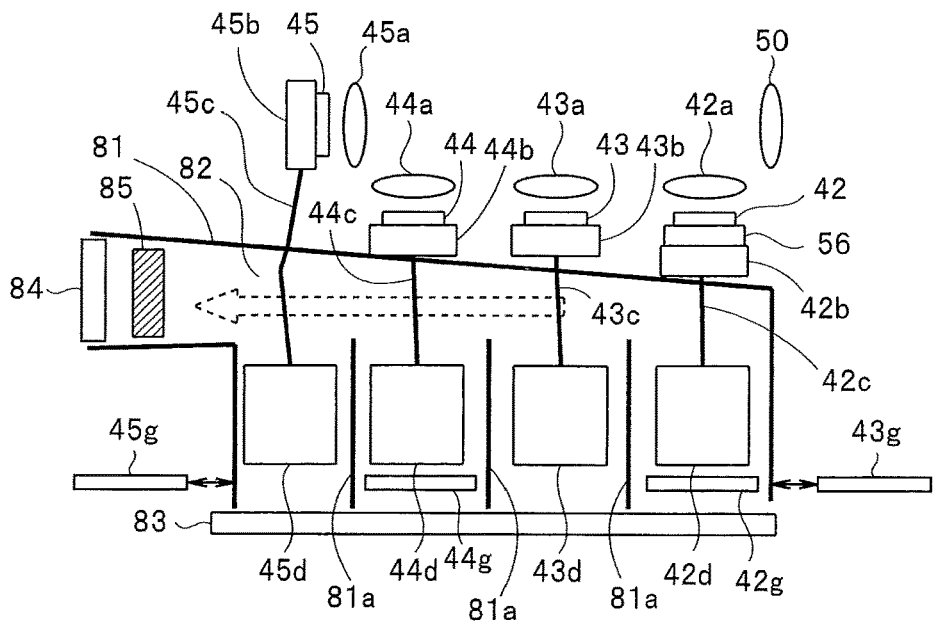
FIG. 9 is an explanatory diagram for illustrating another example of the cooling structure.

FIG. 9 is an explanatory diagram for illustrating another example of the cooling structure. In FIG. 9, same components as those in FIG. 4 are given same reference numerals, and description of the components will be omitted.

In the example of FIG. 9, an arrangement area of the respective LEDs 42 to 45 and a heat radiation route are separated by a separating wall 81 in a case of a light source apparatus. In the example of FIG. 9, heat radiation routes of cooling members for respective LEDs are separated by walls 81a similarly to the example of FIG. 4. In the example of FIG. 4, the fans 42e to 45e are provided between the respective heat sinks 42d to 45d and the inlet port 63. In the example of FIG. 9, the fans 42e to 45e are omitted; one fan 85 is provided in front of an exhaust port 84; and flow path restricting members 42g to 45g can be arranged between the respective heat sinks 42d to 45d and an inlet port 83, respectively.

The flow path restricting members 42g to 45g are adapted to be driven to freely advance and retract by a driving portion not shown so that a part of the inlet port 83 is blocked. The control portion 41 controls the driving portion not shown to drive the flow path restricting members 42g to 45g to advance and retract to control the flow rates of the heat radiation routes.

By individually removing the flow path restricting members 42g to 45g arranged between the respective heat sinks 42d to 45d and the inlet port 83 while causing the fan 85 to rotate, air flows from the inlet port 83 to the exhaust port 84 occur at positions where the flow path restricting members 42g to 45g are removed. On the contrary, by individually arranging the flow path restricting members 42g to 45g between the respective heat sinks 42d to 45d and the inlet port 83, it becomes difficult for air from the inlet port 83 to the exhaust port 84 to flow at the positions where the heat sinks 42d to 45d are arranged.

The heat radiation routes separated by the walls 81a are integrated into one heat radiation route 82 near the separating wall 81. When a part of the flow path restricting members 42g to 45g are arranged at the inlet port 83, flow rates of air increase at positions where a flow path restricting member is not arranged, if rotation of the fan 85 is same. Therefore, for example, at the time of the special-light observation, it is possible to, by arranging flow path restricting members so that positions at the inlet port 83 corresponding to the LEDs 42 and 44 are blocked, cause amounts of air passing through the heat sinks 45d and 43d corresponding to the V-LED 45 and the G-LED 43 which are lit up, absorbing heat of the heat sinks 45d and 43d, to increase without changing the rotation of the fan 85. Therefore, at the time of the special-light observation, it is possible to decrease the number of rotations of the fan 85 in comparison with the time of the normal-light observation, and reduce power consumption and noise caused by the fan.

(Second Embodiment)

Figure 10:
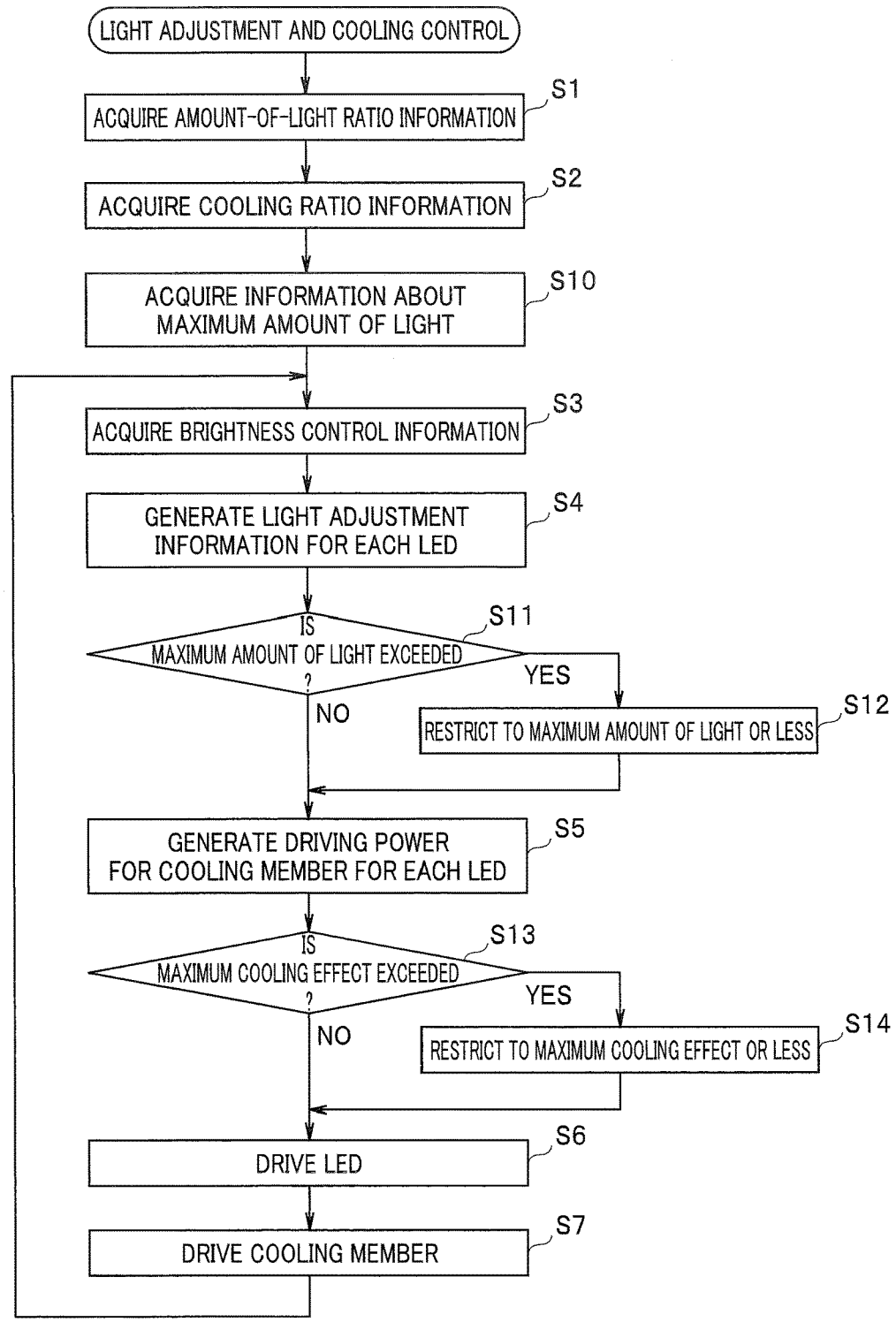
FIG. 10 is a flowchart adopted in a second embodiment of the present invention.

FIG. 10 is a flowchart adopted in a second embodiment of the present invention. In FIG. 10, same procedures as those in FIG. 6 are given same reference numerals, and description of the procedures will be omitted. A hardware configuration of the present embodiment is similar to FIG. 1. In the first embodiment, the control portion 41 determines a cooling ratio based on information about an amount-of-light ratio and controls power supply to cooling members for respective LEDs so that the determined cooling ratio is obtained. However, an amount of light which can be caused to be incident on or can be emitted from the light guide 15 used in the endoscope 10, is restricted depending on a kind or diameter of the light guide 15. Further, in order to prevent occurrence of halation when the image pickup device 13 performs image pickup also, it is necessary that an amount of emitted light of the light source apparatus 40 be restricted to be a predetermined maximum value (a maximum amount of light) or less. That is, it is necessary to set the amounts of emitted light of the respective LEDs 42 to 45 to predetermined upper-limit values or less, respectively, and, therefore, it is also necessary to restrict cooling capacities of the cooling members for cooling the LEDs 42 to 45, respectively.

Information about such maximum amount of light is stored in the storage portion 19 of the endoscope 10, and the reading portion 51 is adapted to read the information about the maximum amount of light from the storage portion 19 and supplies the information to the control portion 41. The control portion 41 is adapted to restrict maximum amounts of emitted light of the respective LEDs 42 to 45 based on the information about the maximum amount of light.

Note that, though the maximum amount of emitted light of the light source apparatus 40, that is, synthesized light of the LEDs 42 to 45 is restricted, an upper-limit value of the maximum amount of light can be determined for each LED because the amount-of-light ratio of the LEDs 42 to 45 is determined. Therefore, information about the maximum amount of light permitted for a predetermined LED may be used as the information about the maximum amount of light.

Further, by causing information about the maximum amount of light for each endoscope and for each observation mode to be stored in the memory portion 57, only information about the model number of an endoscope and information about which observation is selected may be caused to be stored in the storage portion 19. As the information about the maximum amount of light, the information about the model number of an endoscope, the information about which observation is used, and the like are included.

Further, in order to restrict the maximum amount of light, it is only necessary to input information about the maximum amount of light suitable for an endoscope or an observation mode to the control portion 41, and it is not necessarily required to provide the storage portion 19 and the reading portion 51. For example, it is also possible to input the information about the maximum amount of light by using the operation panel 52.

Further, there may be a case where an endoscope not holding such information about the maximum amount of light is adopted as the endoscope 10. In this case, the control portion 41 may control the amounts of light emission of the respective LEDs 42 to 45 to be predetermined amounts of light or less.

In the present embodiment, the control portion 41 is given the information about the maximum amount of light, and decides the upper-limit values of the cooling capacities (maximum cooling capacities) of the cooling members corresponding to the respective LEDs. The control portion 41 determines power (maximum power) in a case of causing a cooling member for each LED to demonstrate a maximum cooling capacity, and performs control to drive the cooling member with the maximum power or lower.

At step S10 in FIG. 10, the control portion 41 acquires the information about the maximum amount of light. At step S4, the control portion 41 determines control values for the respective LEDs and generates light adjustment information for specifying the control values. At step S11, the control portion 41 judges whether the maximum amount of light is exceeded if the control values determined at step S4 are set for the respective LEDs 42 to 45. The amounts of emitted light of the respective LEDs 42 to 45 in the case where the control values are set for the respective LEDs 42 to 45, respectively, are already known, and, therefore, the control portion 41 can determine the amounts of emitted lights of the LEDs 42 to 45 and the amount of light synthesized by the respective emitted lights by calculation.

If the amount of light determined by calculation exceeds the maximum amount of light given by the information about the maximum amount of light, the control portion 41 causes the process to proceed to step S12 to restrict the control values to be such values that an amount of light equal to or less than the maximum amount of light is obtained. Thereby, the amount of light of the emitted light of the light source apparatus 40 is restricted to be the maximum amount of light or less.

Note that, though the control portion 41 has been described as such that controls the light synthesized by the emitted lights of the respective LEDs 42 to 45 to be the maximum amount of light or less, the control portion 41 may perform control so that the amounts of light of any one or plurality of LEDs among the respective LEDs 42 to 45 become the maximum amount of light permitted for the LEDs or less because the amount-of-light ratio of the respective LEDs 42 to 45 is specified.

At step S5, the control portion 41 determines driving powers for the cooling members for the respective LEDs. At step S13, the control portion 41 judges whether the cooling capacities of the respective LEDs exceed the maximum cooling capacities when the driving powers determined at step S5 are set for the respective cooling members. Cooling capacities in the case where the driving powers are set for the cooling members corresponding to the respective LEDs 42 to 45, respectively, are already known, and, therefore, the control portion 41 can determine the cooling capacities of the cooling members corresponding to the LEDs 42 to 45 by calculation.

If the cooling capacities determined by calculation exceed the maximum cooling capacities given by the information about the maximum amount of light, the control portion 41 causes the process to proceed to step S14 to restrict the driving powers to be such values that cooling capacities equal to or lower than the maximum cooling capacities are obtained. Thereby, the cooling capacities for the respective LEDs 42 to 45 are restricted to the maximum cooling capacities or lower, and temperatures of the respective LEDs 42 to 45 are maintained within a predetermined temperature range.

Note that, though an example has been described above in which the control portion 41 determines the respective amounts of light of the LEDs 42 to 45 and the amount of synthesized light by calculation, an optical sensor for actually detecting the amounts of light of the respective LEDs 42 to 45 and the amount of synthesized light may be provided. In this case, whether the maximum amount of light is exceeded or not may be judged by actual measurement values of the optical sensor at step S11. There is a possibility that, for reasons such as variation of temperature characteristics of an LED, the amount of light of the LED for a control value may vary. Therefore, by measuring the actual amount of light by the optical sensor, it is possible to accurately determine the amount of light and enable high-precision control.

Further, though description has been made above on an example in which the control portion 41 determines the cooling capacities of the cooling members corresponding to the LEDs 42 to 45 by calculation, it is also possible to use the thermistors 53 to actually detect the temperatures of the respective LEDs 42 to 45 and judge the cooling capacities. In this case, it is possible to judge whether or not the temperatures of the LEDs are equal to or below a predetermined lower-limit value by actually measured values of the thermistors 53 at step S13 and control power supply to the cooling members at step S14.

In this case, the cooling capacities are controlled by actually measuring the temperatures of the LEDs, and, therefore, higher-precision cooling control is possible.

Thus, in the present embodiment, amounts of emitted light and cooling capacities are restricted according to an endoscope or an observation mode, and it is possible to prevent occurrence of an excessive amount of light and prevent an excessive cooling capacity from being demonstrated. Thereby, it is possible to suppress power consumption and noise.

By the way, in the above embodiment, description has been made on a case where the respective LEDs 42 to 45 are driven with amounts of light equal to or less than maximum amounts of light. On the contrary, there may be a case where it is desired to increase the amounts of light of the LEDs 42 to 45. In an LED, inputted power is restricted so that junction temperature is equal to or below a predetermined threshold, in order to suppress deterioration of elements of the LED. The junction temperature has a correlation with ambient temperature, and becomes higher as the ambient temperature is higher. Therefore, in general, upper-limit temperature is set as the ambient temperature, and an upper limit of power inputted to the LED is set based on the junction temperature at time of the set upper-limit ambient temperature.

Figure 11:
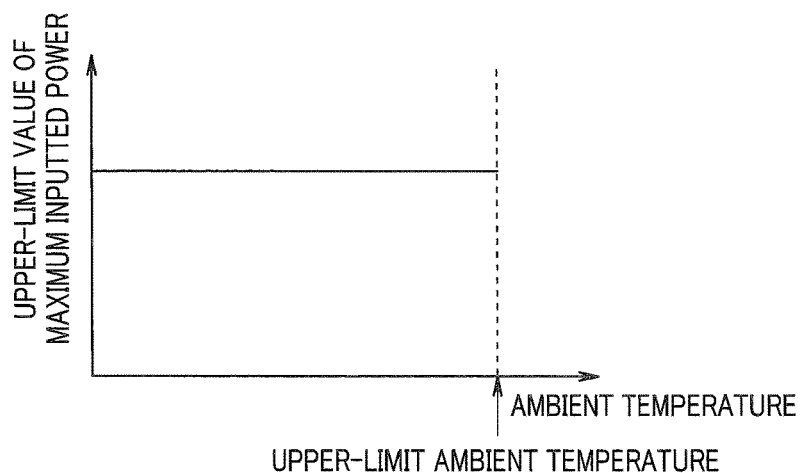
FIG. 11 is a graph showing, when ambient temperature and an upper-limit value of power inputted to an LED are indicated by a horizontal axis and a vertical axis, respectively, a relationship between actual ambient temperature and power inputted to the LED in this case.

FIG. 11 is a graph showing, when ambient temperature and an upper-limit value of power inputted to an LED are indicated by a horizontal axis and a vertical axis, respectively, a relationship between actual ambient temperature and power inputted to the LED in this case. In the example of FIG. 11, since an upper-limit value of maximum inputted power for the LED is specified on an assumption that ambient temperature is upper-limit ambient temperature irrespective of actual ambient temperature, the upper-limit value of the maximum inputted power for the LED is a constant value.

However, when the actual ambient temperature is low, junction temperature is also low, and, therefore, there is no problem even if the power inputted to the LED is increased. Therefore, in each of the above embodiments, it is possible to, by changing the upper-limit value of the maximum inputted power for the LED based on the ambient temperature, increase the amount of light by increasing power which can be supplied to the LED.

In FIG. 1, the thermistors 53 measure temperatures near the LEDs 42 to 45, and the thermistor 54 measures ambient temperature. The control portion 41 is given temperature measurement results of the thermistors 53 and 54, and changes upper-limit values of maximum inputted powers for the LEDs based on the temperature measurement results.

Note that it is better not to be influenced by heat radiation routes of the cooling members or emitted lights of the respective LEDs at time of measuring the ambient temperature. Therefore, it is better to set up the thermistors 53 and 54 at places other than the heat radiation routes where emitted lights of the LEDs 42 to 45 are not applied.

Figure 12:
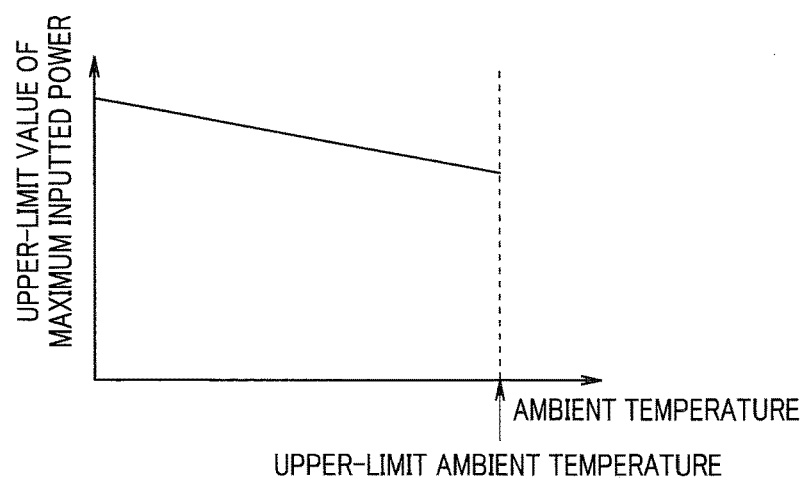
FIG. 12 is a graph showing, when ambient temperature and an upper-limit value of power inputted to an LED are indicated by a horizontal axis and a vertical axis, respectively, a relationship between actual ambient temperature and power inputted to the LED in this case.

FIG. 12 is a graph showing, when ambient temperature and an upper-limit value of power inputted to an LED are indicated by a horizontal axis and a vertical axis, respectively, a relationship between actual ambient temperature and power inputted to the LED in this case. In the example of FIG. 12, since an upper-limit value of maximum inputted power for the LED is specified according to the actual ambient temperature, the upper-limit value of the maximum inputted power for the LED changes, increasing accompanying decrease in the ambient temperature.

Thereby, it is possible to increase the maximum value of the power inputted to the LED according to the ambient temperature, and increase an amount of light emitted from the LED.

By the way, when a temperature characteristic of an LED is considered, it is necessary to use the LED within a predetermined temperature range. When power inputted to the LED is increased, temperature increases accompanying the increase in the inputted power. Therefore, the LED is cooled with use of a Peltier element or the like to use the LED within a predetermined temperature range. However, when the LED is cooled by the Peltier element, temperature of a cooled part becomes lower than the ambient temperature, and there is a possibility that dew condensation may occur. Therefore, in general, a cooling capacity by the Peltier element is restricted so that the temperature of the cooled part does not become lower than ambient temperature, in order to prevent occurrence of dew condensation. That is, an upper-limit value of maximum inputted power for the LED is required to be set according to upper-limit ambient temperature assumed as the maximum value of the ambient temperature even if the Peltier element is adopted, and, therefore, the upper-limit value is a predetermined fixed value.

It is conceivable, however, that dew condensation may not occur depending on an amount of ambient moisture even if the temperature is below the ambient temperature. Therefore, in each of the above embodiments, it is possible to, by changing an upper-limit value of maximum inputted power for an LED based on ambient temperature and ambient humidity, increase power which can be supplied to the LED to increase the amount of light.

Figure 13:
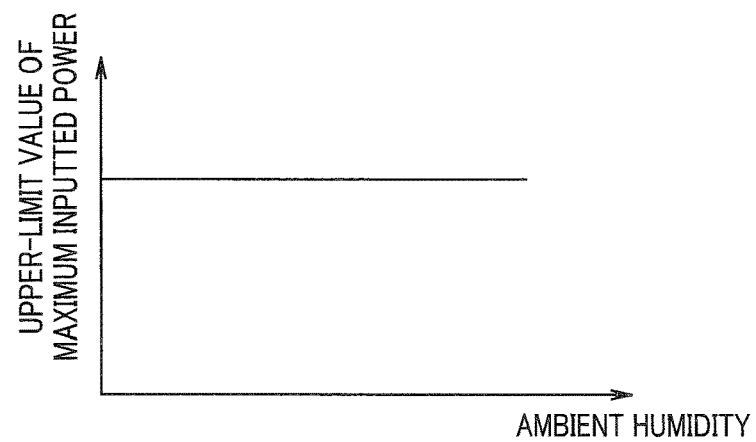
FIG. 13 is a graph showing power inputted to an LED in a predetermined ambient temperature environment, when ambient humidity and an upper-limit value of the power inputted to the LED are indicated by a horizontal axis and a vertical axis, respectively.

FIG. 13 is a graph showing power inputted to an LED in a predetermined ambient temperature environment, when ambient humidity and an upper-limit value of the power inputted to the LED are indicated by a horizontal axis and a vertical axis, respectively. In the example of FIG. 11, humidity is not considered, and it is shown that an upper-limit value of maximum inputted power for an LED is specified for a predetermined ambient temperature. The upper-limit value of the maximum inputted power for the LED is a constant value. Note that, though it is possible to change the upper-limit value of the maximum inputted power for the LED according to the ambient temperature by measuring the ambient temperature, the upper-limit value of the maximum inputted power for the LED is a constant value when the ambient temperature is the same, even if the humidity is relatively low.

In FIG. 1, ambient temperature is measured by the thermistors 53 and 54, and humidity near the Peltier element 56 (ambient humidity) is measured by a humidity sensor not shown. The control portion 41 is given temperature measurement results of the thermistors 53 and 54 and an ambient humidity measurement result by the humidity sensor. Further, it is assumed that a lookup table for an amount of saturated water-vapor allowable for each ambient temperature is stored in the memory portion 57. By referring to the lookup table stored in the memory portion 57, the control portion 41 determines an amount of moisture at the measured ambient temperature and humidity. By comparing the amount of moisture and the amount of saturated water-vapor allowable for each ambient temperature, the control portion 41 determines temperature at which it is possible to perform cooling by the Peltier element 56 without occurrence of dew condensation. The control portion 41 decides an upper-limit value of maximum inputted power for an LED according to the temperature at which cooling is possible.

Figure 14:
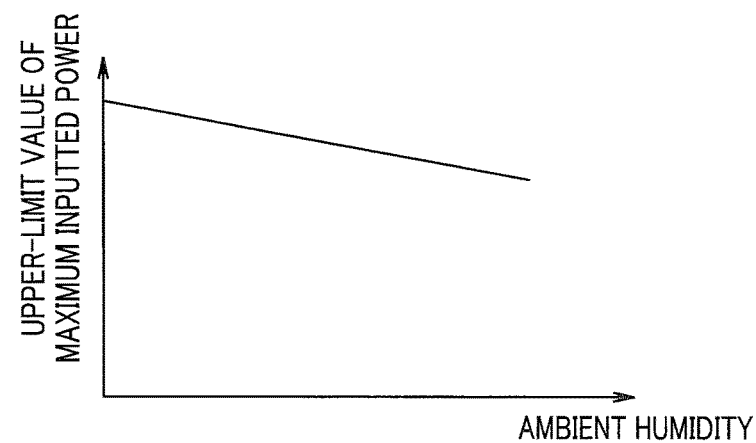
FIG. 14 is a graph showing a relationship between ambient humidity and power inputted to an LED at a predetermined ambient temperature, when the ambient humidity and an upper-limit value of the power inputted to the LED are indicated by a horizontal axis and a vertical axis, respectively.

FIG. 14 is a graph showing a relationship between ambient humidity and power inputted to an LED at a predetermined ambient temperature, when the ambient humidity and an upper-limit value of the power inputted to the LED are indicated by a horizontal axis and a vertical axis, respectively. In the example of FIG. 14, the temperature of cooling by the Peltier element 56 is set according to actual ambient humidity, and relatively low temperature can be set by the Peltier element 56. Therefore, the upper-limit value of maximum inputted power for the LED changes, increasing accompanying decrease in the ambient humidity.

Thereby, it is possible to increase the maximum value of the power inputted to the LED according to ambient humidity, and increase an amount of light emitted from the LED.

Though description has been made on an LED as an example of a solid-state light-emitting element in each of the above embodiments, a laser light source may be used. Further, the present invention is not limited to each of the embodiments as it is, but components can be modified and embodied at an implementation stage within a range not departing from the spirit of the present invention. Further, various inventions can be formed by appropriately combining a plurality of components disclosed in each of the embodiments described above. For example, some components among all components shown in an embodiment may be deleted. Furthermore, components from different embodiments may be appropriately combined.

What is claimed is:
1. An endoscope apparatus comprising:
a first light source configured to generate light;
a second light source configured to generate light;

a first cooling member configured to cool the first light source, a cooling capacity of the first cooling member varying depending on a volume of inputted driving power;
second cooling member configured to cool the second light source, a cooling capacity of the second cooling member varying depending on a volume of inputted driving power;
a light guide configured to:
 be inserted into a subject;
 guide the light from the first light source and the light from the second light source; and
 emit the guided lights as illuminating light from a distal end of the light guide;
an image sensor configured to receive light from the subject to which the illuminating light emitted from the distal end of the light guide is radiated to generate a picked-up image;
a video processor configured to generate brightness control information for controlling an amount of the illuminating light; and
a control portion controller configured to:
 obtain information about an amount-of-light ratio, which is a ratio of an amount of the light emitted by the second light source to an amount of the light emitted by the first light source, and the brightness control information;
 control amounts of light emission of the first light source and the second light source while maintaining an amount-of-light ratio corresponding to the information about the amount-of-light ratio;
 determine respective cooling capacities for the first cooling member and the second cooling member based on the information about the amount-of-light ratio and the brightness control information; and
 control the driving power to be inputted to the first cooling member and the driving power to be inputted to the second cooling member so that the first and second cooling members have the determined cooling capacities,
 wherein, when the control portion obtains, as the information about the amount-of-light ratio, information about a first amount-of-light ratio in which the ratio of the amount of the light emitted by the second light source to the amount of the light emitted by the first light source is a first value, the control portion is configured to:
  obtain information about a first cooling ratio, which is a ratio of the cooling capacity to be set to the first cooling member to the cooling capacity to be set to the second cooling member, based on the information about the first amount-of-light ratio;
  determine the cooling capacity of the first cooling member and the cooling capacity of the second cooling member for cooling, at the first cooling ratio, the first light source and the second light source for which the amounts of light emission are controlled, so as to cause the first light source and the second light source to have a temperature within a predetermined temperature range, based on the brightness control information and the information about the first cooling ratio, and
 wherein, when the control portion obtains, as the information about the amount-of-light ratio, information about a second amount-of-light ratio in which the ratio of the amount of the light emitted by the second light source to the amount of the light emitted by the first light source is a second value different from the first value, the control portion is configured to:
  obtain information about a second cooling ratio, which is a ratio of the cooling capacity to be set to the first cooling member to the cooling capacity to be set to the second cooling member, based on the information about the second amount-of-light ratio; and
  determine the cooling capacity of the first cooling member and the cooling capacity of the second cooling member for cooling, at the second cooling ratio, the first light source and the second light source for which the amounts of light emission are controlled, so as to cause the first light source and the second light source to have a temperature within a predetermined temperature range, based on the brightness control information and the information about the second cooling ratio.

2. The endoscope apparatus according to claim 1, wherein the control portion is configured to read the information about the amount-of-light ratio stored in a storage portion of an endoscope to which illuminating light by the first light source portion and the second light source portion is supplied.

3. The endoscope apparatus according to claim 1, wherein the control portion is configured to control the cooling capacities of the first cooling member and the second cooling member at a predetermined cooling ratio if the information about the amount-of-light ratio is not given.

4. The endoscope apparatus according to claim 1, wherein the information about the amount-of-light ratio is set for each endoscope supplied with the illuminating light by the first light source and the second light source or for each observation mode of the endoscope.

5. The endoscope apparatus according to claim 1, wherein the control portion is configured to:
 perform light emission control of the first light source and the second light source individually so that each of the first light source and the second light source emits light within a permitted predetermined amount of light emission, and
 perform cooling control of the first cooling member and the second cooling member individually so that each of the first cooling member and the second cooling member performs cooling within a permitted cooling capacity.

* * * * *